United States Patent
Aissaoui et al.

(10) Patent No.: US 9,850,241 B2
(45) Date of Patent: *Dec. 26, 2017

(54) AZAINDOLE ACETIC ACID DERIVATIVES AND THEIR USE AS PROSTAGLANDIN D2 RECEPTOR MODULATORS

(71) Applicant: IDORSIA PHARMACEUTICALS LTD, Allschwil (CH)

(72) Inventors: Hamed Aissaoui, Allschwil (CH); Christoph Boss, Allschwil (CH); Patrick Bouis, Allschwil (CH); Julien Hazemann, Allschwil (CH); Romain Siegrist, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/127,361

(22) PCT Filed: Mar. 17, 2015

(86) PCT No.: PCT/IB2015/051932
§ 371 (c)(1),
(2) Date: Sep. 19, 2016

(87) PCT Pub. No.: WO2015/140701
PCT Pub. Date: Sep. 24, 2015

(65) Prior Publication Data
US 2017/0129884 A1  May 11, 2017

(30) Foreign Application Priority Data
Mar. 18, 2014 (WO) .................. PCT/IB2014/059927

(51) Int. Cl.
C07D 471/04 (2006.01)
A61K 31/435 (2006.01)

(52) U.S. Cl.
CPC .......... C07D 471/04 (2013.01); A61K 31/435 (2013.01)

(58) Field of Classification Search
CPC ....................... C07D 471/04; A61K 31/435
USPC ............................................ 546/81; 514/290
See application file for complete search history.

(56) References Cited

U.S. PATENT DOCUMENTS

| | | | |
|---|---|---|---|
| 4,808,608 A | 2/1989 | Guindon et al. | |
| 4,965,258 A | 10/1990 | Boshagen et al. | |
| 7,534,897 B2 | 5/2009 | Tanimoto et al. | |
| 7,714,132 B2 | 5/2010 | Fecher et al. | |
| 7,897,788 B2 | 3/2011 | Fecher et al. | |
| 8,039,474 B2 | 10/2011 | Fecher et al. | |
| 8,143,304 B2 | 3/2012 | Fretz et al. | |
| 8,697,869 B2 | 4/2014 | Aissaoui et al. | |
| 9,096,595 B2 | 8/2015 | Aissaoui et al. | |
| 2005/0171143 A1 | 8/2005 | Tanimoto et al. | |
| 2007/0191416 A1 | 8/2007 | Fecher et al. | |
| 2009/0270414 A1 | 10/2009 | Fecher et al. | |
| 2010/0063103 A1 | 3/2010 | Armer et al. | |
| 2010/0190830 A1 | 7/2010 | Fretz et al. | |
| 2010/0234396 A1 | 9/2010 | Fecher et al. | |
| 2011/0311483 A1 | 12/2011 | Jia et al. | |

FOREIGN PATENT DOCUMENTS

| | | |
|---|---|---|
| CN | 103450218 A | 12/2013 |
| EP | 0242516 A1 | 10/1987 |
| EP | 0425908 A2 | 5/1991 |
| EP | 1505061 A1 | 2/2005 |
| EP | 1600440 A1 | 11/2005 |
| EP | 1932839 A1 | 6/2006 |
| EP | 1852420 A1 | 11/2007 |
| EP | 1911759 A1 | 4/2008 |
| EP | 1916245 A1 | 4/2008 |
| GB | 2388540 A | 11/2003 |
| GB | 2407318 A | 4/2005 |
| GB | 2422829 A | 8/2006 |
| GB | 2422830 A | 8/2006 |

(Continued)

OTHER PUBLICATIONS

Myungsoo Joo et al, 2012, PGD Synthase and PGD2 in Immune Response.*
Arimura et al., "Prevention of Allergic Inflammation by a Novel Prostaglandin Receptor Antagonist, S-5751," Journal of Pharmacology and Experimental Therapeutics, vol. 298, 2001, pp. 411-419.
Birkinshaw et al., "Discovery of potent CRTh2 (DP2) receptor antagonists," Bioorganic & Medicinal Chemistry Letters, vol. 16, 2006, pp. 4287-4290.
Fretz et al., "Identification of 2-(2-(1-Naphthoyl)-8-fluoro-3, 4-dihydro-1H-pyrido [4,3-b] indol-5(2H)-yl)acetic Acid (Setipiprant/ACT-129968), a Potent, Selective, and Orally Bioavailable Chemoattractant Receptor-Homologous Molecule Expressed on Th2 Cells Antagonist," J. Med. Chem., vol. 56 2013 pp. 4899-4911.

(Continued)

Primary Examiner — Rita J Desai
(74) Attorney, Agent, or Firm — Arent Fox LLP

(57) ABSTRACT

The present invention relates to azaindolle acetic acid derivatives of formula (I),

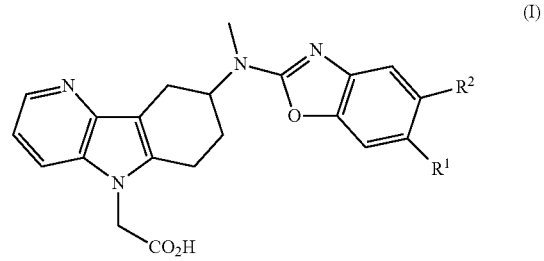

(I)

wherein $R^1$ and $R^2$ are as described in the description and their use as prostaglandin receptor modulators, most particularly as prostaglandin $D_2$ receptor modulators, in the treatment of various prostaglandin-mediated diseases and disorders, to pharmaceutical compositions containing these compounds and to processes for their preparation.

12 Claims, No Drawings

(56) References Cited

FOREIGN PATENT DOCUMENTS

| | | |
|---|---|---|
| GB | 2422831 A | 8/2006 |
| WO | WO 01/78697 A2 | 10/2001 |
| WO | WO 01/79169 A2 | 10/2001 |
| WO | WO 02/094830 A2 | 11/2002 |
| WO | WO 03/051837 A2 | 6/2003 |
| WO | WO 03/062200 A2 | 7/2003 |
| WO | WO 03/066046 A1 | 8/2003 |
| WO | WO 03/066047 A1 | 8/2003 |
| WO | WO 03/097042 A1 | 11/2003 |
| WO | WO 03/097596 A1 | 11/2003 |
| WO | WO 03/101961 A1 | 12/2003 |
| WO | WO 03/101981 A1 | 12/2003 |
| WO | WO 2004/007451 A1 | 1/2004 |
| WO | WO 2004/039807 A1 | 5/2004 |
| WO | WO 2004-078719 A1 | 9/2004 |
| WO | WO 2004/103970 A1 | 12/2004 |
| WO | WO 2004/106302 A1 | 12/2004 |
| WO | WO 2004/111047 A2 | 12/2004 |
| WO | WO 2005/019171 A1 | 3/2005 |
| WO | WO 2005/033099 A2 | 4/2005 |
| WO | WO 2005/040112 A1 | 5/2005 |
| WO | WO 2005/040114 A1 | 5/2005 |
| WO | WO 2005/044260 A1 | 5/2005 |
| WO | WO 2005/054232 A2 | 6/2005 |
| WO | WO 2005/056527 A1 | 6/2005 |
| WO | WO 2005/073234 A2 | 6/2005 |
| WO | WO 2005/094816 A1 | 10/2005 |
| WO | WO 2005/095397 A1 | 10/2005 |
| WO | WO 2005/121141 A1 | 12/2005 |
| WO | WO 2005/123731 A2 | 12/2005 |
| WO | WO 2006/034418 A2 | 3/2006 |
| WO | WO 2006/034419 A2 | 3/2006 |
| WO | WO 2006/036994 A2 | 4/2006 |
| WO | WO 2006/063763 A1 | 6/2006 |
| WO | WO 2006/081343 A1 | 8/2006 |
| WO | WO 2006/090817 A1 | 8/2006 |
| WO | WO 2006/092579 A1 | 9/2006 |
| WO | WO 2006/096183 A1 | 9/2006 |
| WO | WO 2006/125784 A1 | 11/2006 |
| WO | WO 2006/136859 A2 | 12/2006 |
| WO | WO 2007/010964 A1 | 1/2007 |
| WO | WO 2007/010965 A1 | 1/2007 |
| WO | WO 2007/019675 A1 | 2/2007 |
| WO | WO 2007/022501 A2 | 2/2007 |
| WO | WO 2007/029629 A1 | 3/2007 |
| WO | WO 2007/031747 A1 | 3/2007 |
| WO | WO 2007/045867 A1 | 4/2007 |
| WO | WO 2007/065684 A2 | 5/2007 |
| WO | WO 2007/065683 A1 | 6/2007 |
| WO | WO 2007/065924 A1 | 6/2007 |
| WO | WO 2007/068418 A1 | 6/2007 |
| WO | WO 2007/107772 A1 | 9/2007 |
| WO | WO 2007/138282 A2 | 12/2007 |
| WO | WO 2007/144127 A1 | 12/2007 |
| WO | WO 2008/012511 A1 | 1/2008 |
| WO | WO 2008/014186 A1 | 1/2008 |
| WO | WO 2008/017989 A1 | 2/2008 |
| WO | WO 2008/074966 A1 | 6/2008 |
| WO | WO 2006/070325 A2 | 7/2008 |
| WO | WO 2008/078069 A1 | 7/2008 |
| WO | WO 2008/113965 A1 | 9/2008 |
| WO | WO 2009/044134 A1 | 4/2009 |
| WO | WO 2009/044147 A1 | 4/2009 |
| WO | WO 2009/049021 A1 | 4/2009 |
| WO | WO 2009/061676 A2 | 5/2009 |
| WO | WO 2009/063202 A2 | 5/2009 |
| WO | WO 2009/063215 A2 | 5/2009 |
| WO | WO 2009/077726 A1 | 6/2009 |
| WO | WO 2009/090399 A1 | 7/2009 |
| WO | WO 2009/090414 A1 | 7/2009 |
| WO | WO 2009/093026 A1 | 7/2009 |
| WO | WO 2009/093029 A1 | 7/2009 |
| WO | WO 2009/096526 A1 | 8/2009 |
| WO | WO 2009/140642 A2 | 11/2009 |
| WO | WO 2010/006939 A1 | 1/2010 |
| WO | WO 2010/006944 A1 | 1/2010 |
| WO | WO 2010/008864 A2 | 1/2010 |
| WO | WO 2010/031182 A1 | 3/2010 |
| WO | WO 2010/031183 A1 | 3/2010 |
| WO | WO 2010/031184 A1 | 3/2010 |
| WO | WO 2010/039982 A1 | 4/2010 |
| WO | WO 2010/054113 A2 | 5/2010 |
| WO | WO 2010-054114 A2 | 5/2010 |
| WO | WO 2010/085820 A2 | 7/2010 |
| WO | WO 2010/099039 A1 | 9/2010 |
| WO | WO 2010/142934 A1 | 12/2010 |
| WO | WO 2011/006936 A1 | 1/2011 |
| WO | WO 2011/055270 A1 | 5/2011 |
| WO | WO 2011/117798 A1 | 9/2011 |
| WO | WO 2012/009134 A1 | 1/2012 |
| WO | WO 2012/009137 A1 | 1/2012 |
| WO | WO 2012/140612 A1 | 10/2012 |
| WO | WO 2015/140684 A1 | 9/2015 |

OTHER PUBLICATIONS

Gallant et al., "Discovery of MK-7246, a selective CRTH2 antagonist for the treatment of respiratory diseases," Bioorganic & Medicinal Chemistry Letters, vol. 21, 2011, pp. 288-293.

Gehin et al., "A Novel CRTH2 Antagonist: Single- and Multiple-Dose Tolerability, Pharmacokinetics, and Pharmacodynamics of ACT-453859 in Healthy Subjects," The Journal of Clinical Pharmacology, vol. 55, 2015, pp. 787-797.

Ha et al., "Synthesis of Tetrahydrocarbazole Derivatives as Potent Beta-Adrenoceptor Agonists," Bull. Korean Chem. Soc. vol. 25, 2004, pp. 1784-1790.

Ishizuka et al., "Ramatroban (BAY u 3405): A Novel Dual Antagonist of TXA2 Receptor and CRTh 2, a Newly Identified Prostaglandin D2 Receptor," Cardiovascular Drug Reviews, vol. 22, 2004, pp. 71-90.

Luker et al., "Substituted indole-1-acetic acids as potent and selective CRTh2 antagonists-discovery of AZD1981," Bioorganic & Medicinal Chemistry Letters, vol. 21, 2011, pp. 6288-6292.

Molinaro et al., "CRTH2 Antagonist MK-7246: A Synthetic Evolution from Discovery through Development," The Journal of Organic Chem. vol. 77, 2012, pp. 2299-2309.

Pettipher et al., "Update on the Development of Antagonists of Chemoattractant Receptor-Homologous Molecule Expressed on Th2 Cells (CRTH2). From Lead Optimization of Clinical Proof-of-Concept in Asthma and Allergic Rhinitis." J. Med. Chem., vol. 55, 2012, pp. 2915-2931.

Remington, The Science and Practice of Pharmacy, 21st ed. (2005), Part 5, Pharmaceutical Manufacturing, Lippincott Williams & Willkins, pp. 1-5.

Robarge et al., "Isosteric ramatroban analogs: selective and potent CRTH-2 antagonists," Bioogranic & Medicinal Chemistry Letters, vol. 15, 2005, pp. 1749-1753.

Rosentreter et al., "Synthesis and Absolute Configuration of the New Thromboxane Antagonist (3R)-3-(4-Fluorophenylsulfornamido)-1, 2, 3, 4-tetrahydro-9-carbazolepropanoic Acid and Comparison with its Enantiomer," Arzneim.-Forsh./Drug Res., vol. 39, 1989, pp. 1519-1521.

Royer et al., "A novel antagonist of prostaglandin D2 blocks the locomotoion of eosinophils and basophils," Europ. J. Cln. Investigation, vol. 38, 2008, pp. 663-671.

Sandham et al., "7-Azaindole-3-acetic acid derivatives: Potent and selective CRTh2 receptor antagonists," Bioorganic & Medicinal Chemistry Letters, vol. 19, 2009, pp. 4794-4798.

Sawyer et al., "Molecular pharmacology of the human prostaglandin D2 receptor, CRTH2," British Journal of Pharmacology, vol. 137, 2002, pp. 1163-1172.

Stahl et al., Handbook of Pharmaceutical Salts,Properties, Selection and Use, 2008, pp. 1-24.

Stearns et al., "Novel tricyclic antagonists of the prostaglandin D2 receptor DP2 with efficacy in a murine model of allergic rhinitis," Bioorg. Med. Chem. Lett., vol. 19, 2009, pp. 4647-4651.

Sugimoto et al., "An Orally Bioavailable Small Molecule Antagonist of CRTH2, Rarnatroban (BAY u3405), Inhibits Prostaglandin

(56) References Cited

OTHER PUBLICATIONS

D2-Induced Eosinophil Migration In Vitro," J. of Pharmacology and Experimental Therapeutics, vol. 305, 2003, pp. 347-352.
Tumey et al., "3-Indolyl sultams as selective CRTh2 antagonists," Bioorganic & Medicinal Chemistry Letters, vol. 20, 2010, pp. 3287-3290.
U.S. Appl. No. 10/514,317, now U.S. Pat. No. 7,534,897, Publication No. US-2005-0171143-A1, filed Nov. 15, 2004.
U.S. Appl. No. 10/598,777, now U.S. Pat. No. 7,714,132, Publication No. US-2007-0191416-A1 filed Sep. 11, 2006.
U.S. Appl. No. 11/722,095, now U.S. Pat. No. 8,039,474, Publication No. US 2009-0270414-A1 filed Jun. 19, 2007.
U.S. Appl. No. 12/625,497, now U.S. Pat. No. 7,750,0274, Publication No. US-2010-0063103-A1 filed Nov. 24, 2009.
U.S. Appl. No. 12/724,946, Publication No. US-2010-0234396-A1 filed Mar. 16, 2010.
U.S. Appl. No. 13/074,995, U.S. Publication No. US-2011-0311483-A1, filed Mar. 29, 2011.
U.S. Appl. No. 15/125,018, filed Sep. 9, 2016.
U.S. Appl. No. 12/376,932, now U.S. Pat. No. 8,143,304, Publication No. US-2010-0190830-A1 filed Feb. 9, 2009.
Ulven et al., "Minor Structural Modifications Convert the Dual TP/CRTH2 Antagonist Ramatroban into a Highly Selective and Potent CRTH2 Antagonist," vol. 48, Feb. 2005, pp. 897-900.
Ulven et al., "Synthesis and in vitro evaluation of a selective antagonist and the corresponding radioligand for the prostaglandin D2 receptor CRTH2," Bioogranic & Medicinal Chemistry Letters, vol. 17, 2007, pp. 5924-5927.
Valdenaire et al., "Evolution of novel tricyclic CRTh2 receptor antagonists from a (E)-2-cyano-3-(1H-indol-3-yl)acrylamide scaffold," Bioorganic & Medicinal Chem. Letters, vol. 23, 2013, pp. 944-948.

\* cited by examiner

AZAINDOLE ACETIC ACID DERIVATIVES AND THEIR USE AS PROSTAGLANDIN D2 RECEPTOR MODULATORS

CROSS REFERENCE TO RELATED APPLICATION

This application is a 35 U.S.C. 371 National Phase of PCT Application No. PCT/IB2015/051932 filed Mar. 17, 2015, which claims priority to PCT Application No. PCT/IB2014/059927 filed Mar. 18, 2014 . The disclosure of these prior applications are hereby incorporated in their entirety by reference.

FIELD OF THE INVENTION

The present invention relates to azaindole acetic acid derivatives of formula (I) and their use as prostaglandin receptor modulators, most particularly as prostaglandin D2 receptor ("DP receptor") modulators, in the treatment of various prostaglandin-mediated diseases and disorders, to pharmaceutical compositions containing these compounds and to processes for their preparation. In particular, such derivatives may be used alone or in pharmaceutical compositions for the treatment of both, chronic and acute allergic/immune diseases/disorders such as asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

BACKGROUND OF THE INVENTION

As a response to allergen exposure in allergic conditions, mast cells are activated and release mediators like histamine, thromboxane A2 (TxA2), cysteinyl leukotrienes (CysLTs) and prostaglandin $D_2$ ($PGD_2$). These mediators interact with their respective receptors and cause physiological effects such as increased vascular permeability, edema, pruritus, nasal and pulmonary congestion, bronchoconstriction, and mucus secretion. An increased vascular permeability for example, allows excessive infiltration of eosinophilic and basophilic leukocytes into the tissue and thus amplifies the allergic response.

Current treatments of allergic diseases comprise agents that can block or otherwise interrupt such interactions, e.g. anti-histamines (histamine H1 receptor antagonists), leukotriene receptor antagonists, beta-adrenergic receptor agonists, and corticosteroids.

Generally, treatments with anti-histamines and leukotriene antagonists are limited in efficacy, and long-term usage of corticosteroids is often associated with unwanted side effects.

$PGD_2$ is an agonist known to act on two G-protein-coupled receptors, the $PGD_2$ receptor DP1 and the recently identified CRTH2 (chemoattractant receptor-homologous molecule expressed on Th2 cells) receptor (also referred to as "DP2 receptor").

Elevated $PGD_2$ levels are considered to cause inflammation as observed in allergic diseases such as allergic rhinitis, allergic asthma, allergic conjunctivitis, atopic dermatitis and the like. Therefore, blocking the interaction of $PGD_2$ with its receptors is considered a useful therapeutic strategy for the treatment of such diseases.

GB 2388540 discloses the use of ramatroban ((3R)-3-(4-fluorobenzene-sulfonamido)-1,2,3,4-tetrahydrocarbazole-9-propionic acid), a TxA2 receptor (also referred to as "TP receptor") antagonist with additional antagonistic activity on CRTH2, for the prophylaxis and treatment of allergic diseases, such as asthma, allergic rhinitis or allergic conjunctivitis. In T. Ishizuka et al., Cardiovascular Drug Rev. 2004, 22(2), 71-90 effects of ramatroban on late-phase inflammation are described. Furthermore, oral bioavailability of ramatroban and its ability to inhibit prostaglandin $D_2$-induced eosinophil migration in vitro has been reported (Journal of Pharmacology and Experimental Therapeutics, 305(1), p.347-352 (2003)).

Azaindole acetic acid derivatives with CRTH2 antagonistic activity have been disclosed in WO 2010/054113, WO 2010/054114 and B. A. Stearns et al., Bioorg. Med. Chem. Lett. 2009, 19, 4647-4651.

WO 2011/117798 and WO 2012/140612 disclose (3-heteroarylamino-1,2,3,4-tetrahydro-9H-carbazol-9-yl)-acetic acid and (7-heteroarylamino-6,7,8,9-tetrahydropyrido[1,2-a]indol-10-yl)acetic acid derivatives, respectively, which derivatives have CRTH2 antagonistic activity.

It has now surprisingly been found that particular azaindole acetic acid derivatives substituted with a halogenated benzoxazol-2-ylamino-group have significantly improved properties in an in-vitro cytotoxicity assay in primary cultured rat hepatocytes. It is thus expected that the present compounds have an improved toxicity profile in-vivo.

DESCRIPTION OF THE INVENTION

1) The present invention relates to azaindole acetic acid derivatives of formula (I),

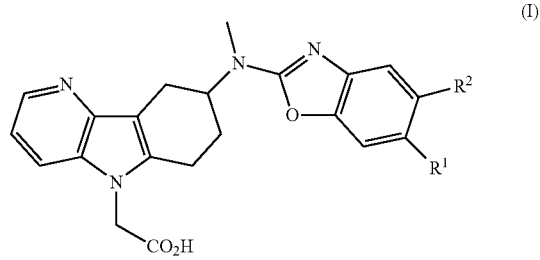

wherein
one of $R^1$ and $R^2$ represents hydrogen and the other one represents halogen;
and to the salts (in particular pharmaceutically acceptable salts) of such compounds.

Definitions provided herein are intended to apply uniformly to the compounds of formula (I) as defined in any one of embodiments 1) to 13), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The compounds of formula (I) as defined in any one of embodiments 1) to 13), may contain one or more stereogenic or asymmetric centers, such as one or more asymmetric carbon atoms. The compounds of formula (I) may thus be present as mixtures of stereoisomers or in stereoisomerically enriched form, preferably as pure stereoisomers. Mixtures of stereoisomers may be separated in a manner known to a person skilled in the art.

The term "enriched", for example when used in the context of enantiomers, is understood in the context of the present invention to mean especially that the respective enantiomer is present in a ratio (mutatis mutandis: purity) of at least 70:30, and notably of at least 90:10 (mutatis mutandis: purity of 70%/90%) with respect to the respective other enantiomer. Preferably the term refers to the respective essentially pure enantiomer. The term "essentially", for example when used in a term such as "essentially pure" is understood in the context of the present invention to mean especially that the respective stereoisomer/composition/compound etc. consists in an amount of at least 90, especially of at least 95, and notably of at least 99 per cent by weight of the respective pure stereoisomer/composition/compound etc.

The term halogen means fluoro, chloro, bromo or iodo; preferred are fluoro and chloro.

2) A further embodiment of the invention relates to compounds of formula (I) according to embodiment 1), wherein $R^1$ represents halogen and $R^2$ represents hydrogen;

and to the salts (in particular pharmaceutically acceptable salts) of such compounds.

3) A further embodiment of the invention relates to compounds of formula (I) according to embodiment 1), wherein $R^1$ represents chloro and $R^2$ represents hydrogen;

and to the salts (in particular pharmaceutically acceptable salts) of such compounds.

4) A further embodiment of the invention relates to compounds of formula (I) according to embodiment 1), wherein $R^1$ represents hydrogen and $R^2$ represents halogen;

and to the salts (in particular pharmaceutically acceptable salts) of such compounds.

5) A further embodiment of the invention relates to compounds of formula (I) according to embodiment 1), wherein $R^1$ represents hydrogen and $R^2$ represents fluoro or chloro;

and to the salts (in particular pharmaceutically acceptable salts) of such compounds.

6) A further embodiment of the invention relates to compounds according to any one of embodiments 1) to 5), wherein the absolute configuration of the stereogenic center is as depicted in formula ($I_{St1}$)

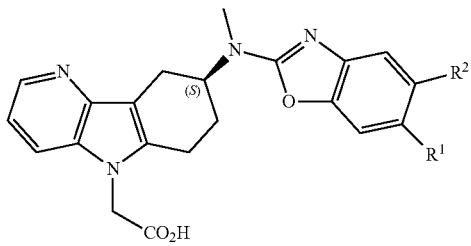

and to the salts (in particular pharmaceutically acceptable salts) of such compounds.

7) A further embodiment of the invention relates to compounds according to any one of embodiments 1) to 5), wherein the absolute configuration of the stereogenic center is as depicted in formula ($I_{St2}$)

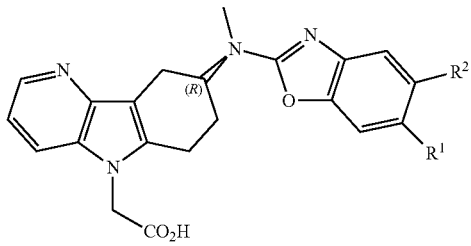

and to the salts (in particular pharmaceutically acceptable salts) of such compounds.

8) Examples of compounds of formula (I) as defined in embodiment 1) are selected from the group consisting of:

2-(8-((5-chlorobenzo[d]oxazol-2-yl) (methyl)amino)-6,7,8,9-tetrahydro-5H-pyrido[3,2-b]indol-5-yl)acetic acid;
2-(8-((5-fluorobenzo[d]oxazol-2-yl)(methyl)amino)-6,7,8,9-tetrahydro-5H-pyrido[3,2-b]indol-5-yl)acetic acid; and
2-(8-((6-chlorobenzo[d]oxazol-2-yl) (methyl)amino)-6,7,8,9-tetrahydro-5H-pyrido[3,2-b]indol-5-yl)acetic acid;

or salts (in particular pharmaceutically acceptable salts) of such compounds;

it is to be understood for any of the above listed compounds, that a stereogenic center, which is not specifically assigned, may be in absolute (R)- or absolute (S)-configuration; for example a compound listed as 2-(8-((6-chlorobenzo[d]oxazol-2-yl)(methyl)amino)-6,7,8,9-tetrahydro-5H-pyrido[3,2-b]indol-5-yl)acetic acid may be (R)-2-(8-((6-chlorobenzo[d]oxazol-2-yl)(methyl)amino)-6,7,8,9-tetrahydro-5H-pyrido[3,2-b]indol-5-yl)acetic acid, (S)-2-(8-((6-chlorobenzo[d]oxazol-2-yl)(methyl)amino)-6,7,8,9-tetrahydro-5H-pyrido[3,2-b]indol-5-yl)acetic acid or any mixture thereof.

9) Preferred examples of compounds of formula (I) as defined in embodiment 1) are selected from the group consisting of:

(S)-2-(8-((5-chlorobenzo[d]oxazol-2-yl)(methyl)amino)-6,7,8,9-tetrahydro-5H-pyrido[3,2-b]indol-5-yl)acetic acid;
(S)-2-(8-((5-fluorobenzo[d]oxazol-2-yl) (methyl)amino)-6,7,8,9-tetrahydro-5H-pyrido[3,2-b]indol-5-yl)acetic acid; and
(S)-2-(8-((6-chlorobenzo[d]oxazol-2-yl) (methyl)amino)-6,7,8,9-tetrahydro-5H-pyrido[3,2-b]indol-5-yl)acetic acid;

or salts (in particular pharmaceutically acceptable salts) of such compounds;

10) In a preferred embodiment the compound of formula (I) as defined in embodiment 1) is:
2-(8-((5-chlorobenzo[d]oxazol-2-yl) (methyl)amino)-6,7,8, 9-tetrahydro-5H-pyrido[3,2-b]indol-5-yl)acetic acid (and notably (S)-2-(8-((5-chlorobenzo[d]oxazol-2-yl)(methyl) amino)-6,7,8,9-tetrahydro-5H-pyrido[3,2-b]indol-5-yl) acetic acid);
or a salt (in particular a pharmaceutically acceptable salt) of the compound;

11) In another preferred embodiment the compound of formula (I) as defined in embodiment 1) is:
2-(8-((5-fluorobenzo[d]oxazol-2-yl)(methyl)amino)-6,7,8, 9-tetrahydro-5H-pyrido[3,2-b]indol-5-yl)acetic acid (and notably (S)-2-(8-((5-fluorobenzo[d]oxazol-2-yl)(methyl) amino)-6,7,8,9-tetrahydro-5H-pyrido[3,2-b]indol-5-yl) acetic acid);
or a salt (in particular a pharmaceutically acceptable salt) of the compound;

12) In another preferred embodiment the compound of formula (I) as defined in embodiment 1) is:
2-(8-((6-chlorobenzo[d]oxazol-2-yl) (methyl)amino)-6,7,8, 9-tetrahydro-5H-pyrido[3,2-b]indol-5-yl)acetic acid (and notably (S)-2-(8-((6-chlorobenzo[d]oxazol-2-yl)(methyl) amino)-6,7,8,9-tetrahydro-5H-pyrido[3,2-b]indol-5-yl) acetic acid);
or a salt (in particular a pharmaceutically acceptable salt) of the compound;

13) The invention, thus, relates to compounds of the formula (I) as defined in embodiment 1), and to such compounds further limited by the characteristics of any one of embodiments 2) to 12), all under consideration of their respective dependencies; to pharmaceutically acceptable salts thereof; and to the use of such compounds as medicaments especially in the treatment of diseases selected from the group consisting of chronic and acute allergic/immune diseases/disorders, comprising asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis. Especially the following embodiments relating to the compounds of formula (I) are thus possible and intended and herewith specifically disclosed in individualized form: 1, 2+1, 3+1, 4+1, 5+1, 6+1, 6+2+1, 6+3+1, 6+4+1, 6+5+1, 7+1, 7+2+1, 7+3+1, 7+4+1, 7+5+1, 8+1, 9+1, 10+1, 11+1, and 12+1; in the list above the numbers refer to the embodiments according to their numbering provided hereinabove whereas "+" indicates the dependency from another embodiment. The different individualized embodiments are separated by commas. In other words, "6+2+1" for example refers to embodiment 6) depending on embodiment 2), depending on embodiment 1), i.e. embodiment "6+2+1" corresponds to the compounds of embodiment 1) further limited by the features of the embodiments 2) and 6)).

Where the plural form is used for compounds, salts, pharmaceutical compositions, diseases or the like, this is intended to mean also a single compound, salt, pharmaceutical composition, disease or the like.

Any reference to a compound of formula (I) as defined in any one of embodiments 1) to 13) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quere (Eds.), RSC Publishing, 2012.

The present invention also includes isotopically labelled, especially 2H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially 2H (deuterium) labelled compounds of formula (I) and salts thereof are within the scope of the present invention. Substitution of hydrogen with the heavier isotope 2H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

The compounds of formula (I) as defined in any one of embodiments 1) to 13) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, The Science and Practice of Pharmacy, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) as defined in any one of embodiments 1) to 13).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as useful for the prevention or treatment of certain diseases, such compounds are likewise suitable for use in the preparation of a medicament for the prevention or treatment of said diseases.

Another aspect of the invention concerns a method for the prevention or the treatment of a disease or disorder as mentioned below in a patient comprising the administration to said patient of a pharmaceutically active amount of a compound of formula (I) as defined in any one of embodiments 1) to 13) or a pharmaceutically acceptable salt thereof.

The compounds of formula (I) according to any one of embodiments 1) to 13), or pharmaceutically acceptable salts thereof, may be used for the preparation of a medicament, and are suitable for the prevention and/or treatment of diseases selected from the group consisting of chronic and acute allergic/immune diseases/disorders, comprising asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

In another embodiment, the compounds of formula (I) according to any one of embodiments 1) to 13), or pharmaceutically acceptable salts thereof, may be used for the preparation of a medicament, and are suitable for the prevention and/or treatment of diseases selected from the group consisting of nasal polyposis, Still's disease (systemic onset juvenile idyiopathic arthritis) and cystic fibrosis.

In a preferred embodiment, the compounds of formula (I) according to any one of embodiments 1) to 13), or pharmaceutically acceptable salts thereof, may be used for the preparation of a medicament, and are suitable for the prevention and/or treatment of diseases selected from the group consisting of asthma, allergic asthma, eosinophilic asthma, severe asthma, allergic rhinitis, angioedema, insect venom allergy, drug allergies, allergic sinusitis, allergic nephritis, allergic conjunctivitis, atopic dermatitis, food allergy, systemic mast cell disorders, anaphylactic shock, urticaria and eczema.

In another preferred embodiment, the compounds of formula (I) according to any one of embodiments 1) to 13), or pharmaceutically acceptable salts thereof, may be used for the preparation of a medicament, and are suitable for the prevention and/or treatment of diseases selected from the group consisting of eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms).

In yet another preferred embodiment, the compounds of formula (I) according to any one of embodiments 1) to 13), or pharmaceutically acceptable salts thereof, may be used for the preparation of a medicament, and are suitable for the prevention and/or treatment of diseases selected from the group consisting of basophil-related diseases, comprising basophilic leukemia and basophilic leukocytosis.

In a most preferred embodiment, the compounds of formula (I) according to any one of embodiments 1) to 13), or pharmaceutically acceptable salts thereof, may be used for the preparation of a medicament, and are suitable for the prevention and/or treatment of diseases selected from the group consisting of asthma, eosinophilic asthma, allergic rhinitis, atopic dermatitis, nasal polyposis, food allergy (notably IgE-mediated food allergy), urticaria (notably chronic urticaria), eosinophilic esophagitis, Churg Strauss Syndrome, hypereosinophilic syndrome, eosinophilic pneumonia (notably chronic eosinophilic pneumonia), DRESS syndrome, Still's disease, COPD and cystic fibrosis (and especially asthma, eosinophilic asthma, allergic rhinitis, atopic dermatitis, IgE-mediated food allergy, chronic urticaria, eosinophilic esophagitis and Churg Strauss Syndrome).

The invention also relates to the use of a compound of formula (I) according to any one of embodiments 1) to 13) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 13).

A pharmaceutical composition according to the present invention contains at least one compound of formula (I) according to any one of embodiments 1) to 13) (or a pharmaceutically acceptable salt thereof) as the active agent and optionally carriers and/or diluents and/or adjuvants.

Any reference to a compound of formula (I), ($I_{ST1}$) or ($I_{ST2}$) in this text is to be understood as referring also to the salts (and especially the pharmaceutically acceptable salts) of such compounds, as appropriate and expedient. The preferences indicated for the compounds of formula (I) of course apply mutatis mutandis to the compounds of formula ($I_{ST1}$) and to the compounds of formula ($I_{ST2}$) as well as to the salts and pharmaceutically acceptable salts of the compounds of formula (I), of formula ($I_{ST1}$) or of formula ($I_{ST2}$). The same applies to these compounds as medicaments, to pharmaceutical compositions containing these compounds as active principles or to the uses of these compounds for the manufacture of a medicament for the treatment of the diseases according to this invention.

As mentioned earlier, compounds of formula (I) modulate as antagonists the $PGD_2$ activation of the CRTH2 receptor. The biological effect of such compounds may be tested in a variety of in vitro, ex vivo and in vivo assays. The ability of the compounds of formula (I) to bind to the CRTH2 receptor may be measured by methods similar to those described in the literature (Arimura A. et al., *J. Pharmacol. Exp. Ther.* 2001, 298(2), 411-419; and Sawyer N. et al., *Br. J. Pharmacol*, 2002, 137, 1163-1172, respectively) and by the assays described below in the experimental part.

A further aspect of the invention is a process for the preparation of compounds of formula (I). Compounds according to formula (I) of the present invention can be prepared according to the sequence of reactions outlined in the schemes below wherein $R^1$ and $R^2$ are as defined for formula (I). Other abbreviations used are defined in the experimental section.

In general, all chemical transformations can be performed according to well-known standard methodologies as described in the literature, or as described in the procedures below. The compounds obtained may also be converted into pharmaceutically acceptable salts thereof in a manner known per se.

The compounds of formula (I) may be prepared from the azaindole derivative (4) which itself may be synthesized by MW irradiation of 3-amino-2-bromo-pyridine (1) with N-methyl-1,4-dioxaspiro[4,5]decan-8-amine (2) in the presence of a catalyst such as $Pd(Ph_3P)_4$ in pyridine. N-methyl-1,4-dioxaspiro[4,5]decan-8-amine (2) may be prepared by reductive amination of commercially available 1,4-dioxaspiro[4,5]decan-8-one (3) with methylamine in the presence of a reducing agent such as $NaBH(OAc)_3$ in an aprotic solvent such as MeCN. Alkylation of the azaindole derivative (4) with ethyl bromoacetate in the presence of of a base such as NaH in an aprotic solvent such as DMF gives the desired azaindole acetic acid ethylester (5); enantiomerically enriched azaindole derivatives (5) may be prepared according to the procedure given in the experimental part. Reaction of amine (5) with the respective 2-chloro-benzoxazole derivative in the presence of a base such as $K_2CO_3$ in an aprotic solvent such as DMA followed by saponification with a base such as NaOH furnished the compounds of formula (I).

Scheme 1: General synthetic route for the preparation of compounds of formula (I)

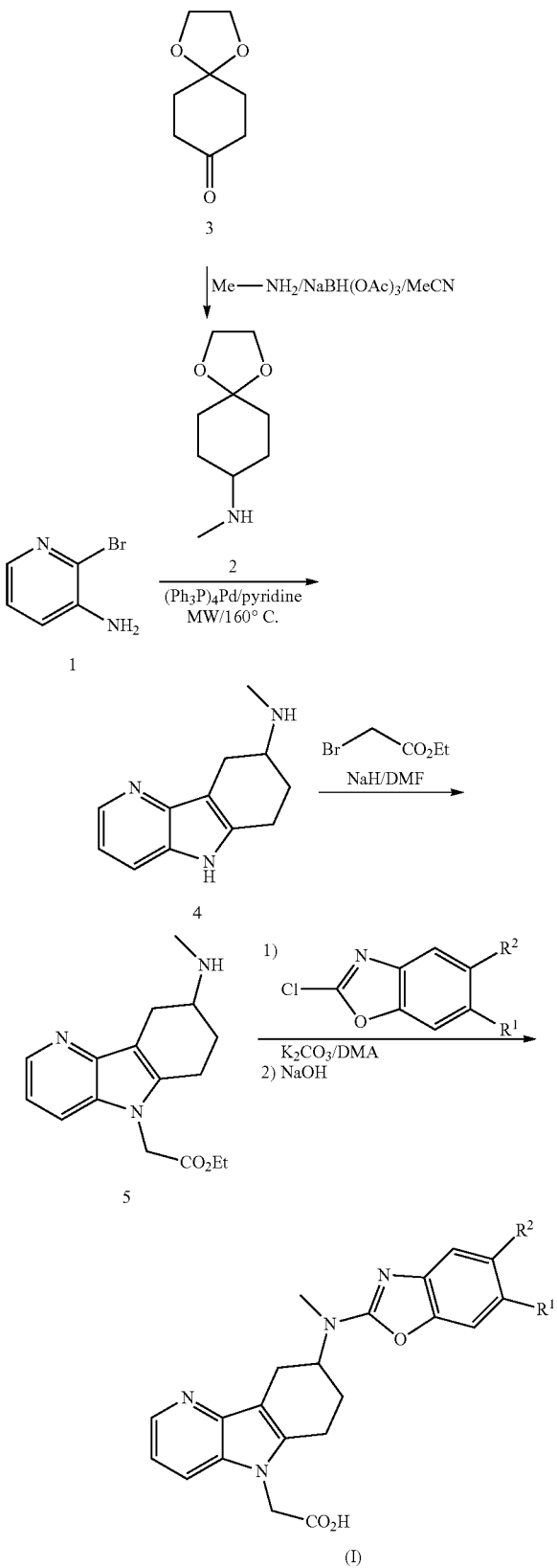

Whenever the compounds of formula (I) or an intermediate of structures 4 or 5 are obtained in the form of mixtures of enantiomers, the enantiomers may be separated using methods known to the one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as TEA and/or DEA) and eluent B (hexane), at a flow rate of 0.8 to 150 mL/min.

Experimental Section:
Abbreviations (As Used Herein):
Ac Acetyl
aq. Aqueous
APC Allophycocyanin
Boc tert-butoxycarbonyl
BSA Bovine Serum Albumin
d Doublet
DCM Dichloromethane
DEA Diethylamine
DMA Dimethylacetamide
DMF Dimethylformamide
DMSO Dimethylsulfoxide
dpm decays per minute
EA Ethyl acetate
EDTA Ethylene Diamine Tetraacetic Acid
eq Equivalent
ESI-MS Electrospray Ionization Mass Spectroscopy
Et Ethyl
FC Flash chromatography
h Hour(s)
HEPES 4-(2-hydroxyethyl)-1-piperazineethanesulfonic acid
HPLC High Performance Liquid Chromatography
HSA Human Serum Albumin
iPrOH Isopropanol
L Liter(s)
LC-MS Liquid ChromatographyMass Spectroscopy
m Multiplet
Me Methyl
MeCN Acetonitrile
min Minute(s)
MS Mass Spectroscopy
MW Microwave
N Normality of solution
NMR Nuclear magnetic resonance
PBS Phosphate Buffered Saline
PEI Polyethyleneimine
$PGD_2$ Prostaglandin $D_2$
Ph Phenyl
Pr Propyl
RT Room temperature
s Second(s)
s Singlet
sat Saturated
t Triplet
tBu tent-butyl
TEA Triethylamine
TFA Trifluoroacetic acid
$t_R$ Retention time
Tris Tris-(hydroxymethyl)aminomethane buffer
Chemistry
General Remarks
All solvents and reagents are used as obtained from commercial sources unless otherwise indicated.

Temperatures are indicated in degrees Celsius (° C.). Unless otherwise indicated, the reactions take place at room temperature (RT).

In mixtures, relations of parts of solvent or eluent or reagent mixtures in liquid form are given as volume relations (v/v), unless indicated otherwise.

Analytical HPLC conditions as used in the Examples below:

HPLC/MS analyses are performed on a Agilent 1100 system, equipped with a Dionex P580 binary pump, a Dionex PDA-100 Photodiode Array Detector and a Finnigan AQA mass spectrometer.

The LC retention times are obtained using the following elution condition:

Analytical HPLC on a Zorbax® SB-AQ column (4.6×50 mm, 3.5 μm, Agilent); Linear gradient of water/0.04% TFA (A) and MeCN (B) from 5% to 95% B over 1.5 min; flow rate 4.5 ml/min, detection at 210 nm.

Preparative HPLC/MS purifications (acidic conditions) are performed on a Gilson 333/334 binary high pressure gradient pump system with a Gilson 215 autosampler and fraction collector, a Dionex UVD340U DAD detector, a polymerlabs PL-ELS 1000 ELS detector and a Thermo MSQ Plus MS detector, using a Waters Atlantis T3 column (10 μm, 30×75 mm), with a linear gradient of water/0.5% formic acid (B) and MeCN (A) starting from 80/20 to 5/95 (B)/(A) over 5 min.; flow rate 75 ml/min.

Preparative HPLC/MS purifications (basic conditions) are performed on a Gilson 333/334 binary high pressure gradient pump system with a Gilson 215 autosampler and fraction collector, a Dionex UVD340U DAD detector, a polymerlabs PL-ELS 1000 ELS detector and a Thermo MSQ Plus MS detector, using a Waters XBridge C18 column (10 μm, 30×75 mm), with a linear gradient of water/0.5% 25% $NH_4OH$ (B) and MeCN (A) starting from 80/20 to 5/95 (B)/(A) over 5 min.; flow rate 75 ml/min.

Analytical HPLC over a chiral stationary phase are performed on a Daicel ChiralPak AD-H (4.6×250 mm, 5 μm) column or a Chiralpak AY-H (4.6×250 mm, 5 μm) column. Typical conditions of chiral HPLC are an isocratic mixture of 30% heptane+0.05% DEA and 70% EtOH+0.05% DEA, at a flow rate of 0.8 mL/min., detection at 210 nm (chiral HPLC-1) or an isocratic mixture of 40% heptane and 60% EtOH+0.1% TFA, at a flow rate of 1.0 mL/min., detection at 210 nm (chiral HPLC-2).

Preparative HPLC over a chiral stationary phase are performed on a Daicel ChiralPak AD-H (20×250 mm, 5 μm) column. Typical conditions of chiral HPLC are an isocratic mixture of 50% EtOH and 50% heptane, at a flow rate of 16 mL/min., detection at 210 nm (chiral HPLC-3).

A. Synthesis of 2-(8-((benzo[d]oxazol-2-yl)(methyl) amino)-6,7,8,9-tetrahydro-5H-pyrido[3,2-b]indol-5-yl)acetic acid derivatives A.1. Synthesis of N-methyl-1,4-dioxaspiro[4,5]decan-8-amine A mixture of 1,4-dioxaspiro[4,5]decan-8-one (1.0 eq), methylamine (8M in EtOH, 1.0 eq), and $NaBH(OAc)_3$ (3.0 eq) in MeCN (10 mL/6.2 mmol) was stirred at RT for 20 h. The reaction mixture was then concentrated in vacuo, dissolved in a mixture EN iPrOH (4/1) and washed with sat. $NaHCO_3$ and brine. The aqueous phase was extracted with EA/iPrOH (4/1). The combined organic extracts were dried (MgSO₄), filtered and concentrated in vacuo to give the desired product which was used in the next step without further purification.

¹H-NMR (CDCl₃) δ: 1.35 (m, 2H); 1.45 (m, 2H); 1.75 (m, 2H); 1.95 (m, 2H); 3.45 (m, 4H); 3.95 (s, 4H)

A.2. Synthesis of N-methyl-6,7,8,9-tetrahydro-5H-pyrido[3,2-b]indol-8-amine

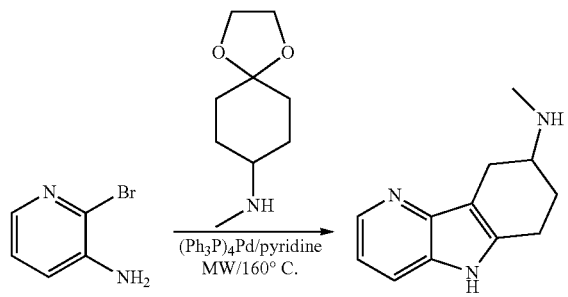

A solution of 3-amino-2-bromopyridine (1.0 eq), N-methyl-1,4-dioxaspiro[4,5]decan-8-amine (1.2 eq) and (Ph₃P)₄Pd (0.05 eq) in pyridine (1 mL/0.07 mmol) was irradiated by MW at 160° C. for 1 h. After cooling at RT, the reaction mixture was poured into water and extracted with EA. The combined organic extracts were concentrated in vacuo and the residue was purified by prep. HPLC (basic conditions) to provide the desired compound.

LC-MS: $t_R$=0.37 min; [M+H]⁺=202.21.

A.3 Synthesis of ethyl 2-(8-(methylamino)-6,7,8,9-tetrahydro-5H-pyrido[3,2-b]-indol-5-yl)acetate

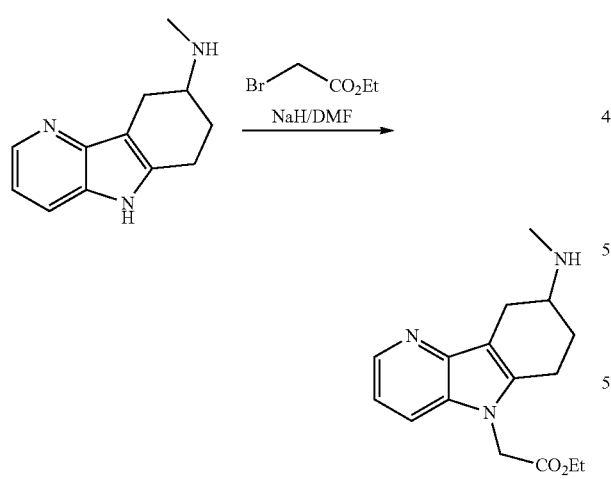

To a cold (0° C.) solution of N-methyl-6,7,8,9-tetrahydro-5H-pyrido[3,2-b]indol-8-amine (1.0 eq) in dry DMF (1 mL/0.04 mmol), was added NaH (1.1 eq, 60% dispersion in mineral oil). The reaction mixture was stirred at 0° C. for 10 min, ethyl bromoacetate (1.0 eq) was added and the reaction mixture was allowed to warm to RT and stirred overnight. Water was added and the reaction mixture was directly purified by prep-HPLC (basic conditions) to provide the desired compound.

LC-MS: $t_R$=0.38 min; [M+H]⁺=288.28.

A.4 Synthesis of 2-(8-((benzo[d]oxazol-2-yl)(methyl)amino)-6,7,8,9-tetrahydro-5H-pyrido[3,2-b]indol-5-yl)acetic acid derivatives General Procedure:

A mixture of ethyl 2-(8-(methylamino)-6,7,8,9-tetrahydro-5H-pyrido[3,2-b]-indol-5-yl)acetate (0.06 mmol), the respective 2-chloro-benzo[d]oxazole derivative (0.06 mmol) and K₂CO₃ (0.24 mmol) in DMA (0.5 mL) was stirred at 80° C. for 12 h. After cooling to RT, water (0.07 mL) and 30% aq NaOH (0.07 ml) were added to the reaction mixture. The reaction mixture was stirred at 50° C. for 2 h and then 37% aq HCl (0.07 mL) was added. The products were directly purified by prep. HPLC (acidic conditions) to provide the respective compounds of formula (I).

PREPARATION OF EXAMPLES

The following 2-(8-((benzo[d]oxazol-2-yl)(methyl)amino)-6,7,8,9-tetrahydro-5H-pyrido[3,2-b]indol-5-yl)acetic acid derivatives were synthetized according to the above general procedure.

TABLE 1

| Example | Name | [M + H]⁺ m/z | $t_R$ [min.] LC-MS |
|---|---|---|---|
| 1 | 2-(8-((6-chlorobenzo[d]oxazol-2-yl)(methyl)amino)-6,7,8,9-tetrahydro-5H-pyrido[3,2-b]indol-5-yl)acetic acid | 411.10 | 0.65 |
| 2 | 2-(8-((5-chlorobenzo[d]oxazol-2-yl)(methyl)amino)-6,7,8,9-tetrahydro-5H-pyrido[3,2-b]indol-5-yl)acetic acid | 411.12 | 0.65 |
| 3 | 2-(8-((5-fluorobenzo[d]oxazol-2-yl)(methyl)amino)-6,7,8,9-tetrahydro-5H-pyrido[3,2-b]indol-5-yl)acetic acid | 395.12 | 0.62 |

A.5 Synthesis of ethyl (S)-2-(8-(methylamino)-6,7,8,9-tetrahydro-5H-pyrido[3,2-b]indol-5-yl)acetate

A.5.1 Synthesis of tert-butyl methyl(6,7,8,9-tetrahydro-5H-pyrido[3,2-b]indol-8-yl)carbamate

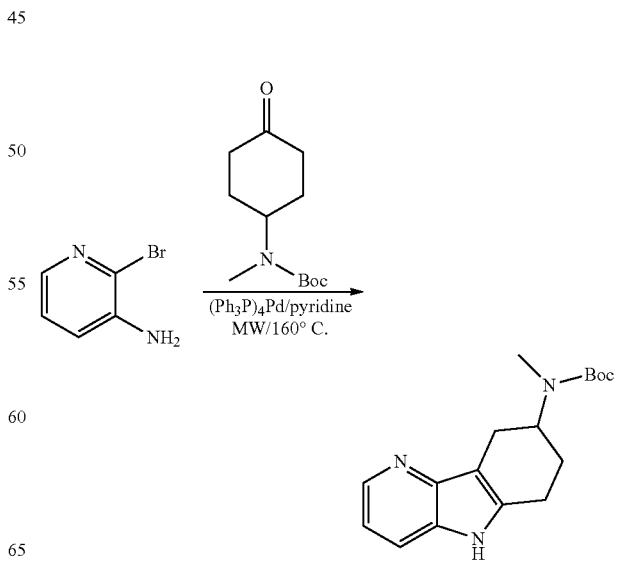

In a vial, 3-amino-2-bromopyridine (2.0 g, 11.6 mmol, 1.0 eq), 4-(N-Boc-N-methylamino)cyclohexanone (3.15 g, 13.9 mmol, 1.2 eq), and (Ph$_3$P)$_4$Pd (668 mg, 0.58 mmol, 0.05 eq) were dissolved in pyridine (7.6 ml). The vial was heated by MW irradiation at 160° C. for 60 min. The reaction mixture was poured into water (9.5 mL) and the resulting solid was collected by filtration, dried, triturated in diethyl ether and collected again by filtration to afford the titled compound.

LC-MS: t$_R$=0.63 min; [M+H]$^+$=302.15.

A.5.2 Synthesis of (S)-ethyl 2-(8-((tert-butoxycarbonyl)(methyl)amino)-6,7,8,9-tetrahydro-5H-pyrido[3,2-b]indol-5-yl)acetate and (R)-ethyl 2-(8-((tert-butoxycarbonyl)(methyl)amino)-6,7,8,9-tetrahydro-5H-pyrido[3,2-b]indol-5-yl)acetate

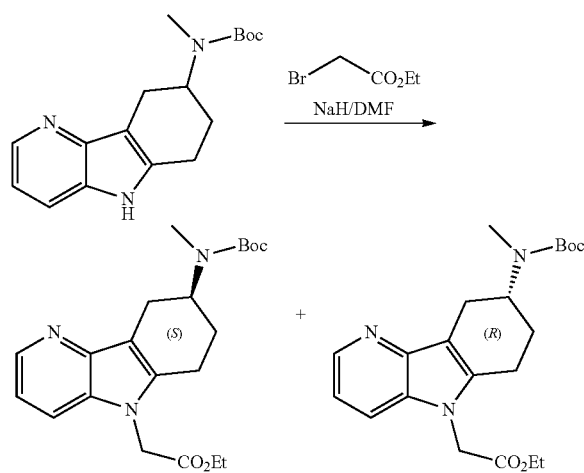

To a cold (0° C.) solution of tent-butyl methyl(6,7,8,9-tetrahydro-5H-pyrido[3,2-b]indol-8-yl)carbamate (1.37 g, 4.56 mmol) in dry DMF (12.5 mL), was added NaH (120 mg, 5.02 mmol, 60% dispersion in mineral oil). The reaction mixture was stirred at 0° C. for 10 min, ethyl bromoacetate (0.52 mL, 4.56 mmol) was added and the reaction mixture was allowed to warm to RT and stirred overnight. Water was added and the resulting precipitate was collected by filtration and washed with water. The crude solid was purified by FC (8% MeOH in DCM) followed by trituration with diethyl ether to provide the desired product as a racemate.

LC-MS: t$_R$: 0.7 min./[M+H]$^+$: 388.50

The two enantiomers of the obtained product were separated by preparative chiral HPLC (chiral HPLC-3):

(R)-ethyl 2-(8-((tert-butoxycarbonyl)(methyl)amino)-6,7,8,9-tetrahydro-5H-pyrido[3,2-b]indol-5-yl)acetate (487 mg, 28%): HPLC (chiral HPLC-1): t$_R$: 6.03 min;

(S)-ethyl 2-(8-((tent-butoxycarbonyl)(methyl)amino)-6,7,8,9-tetrahydro-5H-pyrido[3,2-b]indol-5-yl)acetate (491mg, 28%): HPLC (chiral HPLC-1): t$_R$: 7.36 min.

A.5.3. Synthesis of ethyl (S)-2-(8-(methylamino)-6,7,8,9-tetrahydro-5H-pyrido[3,2-b]indol-5-yl)acetate

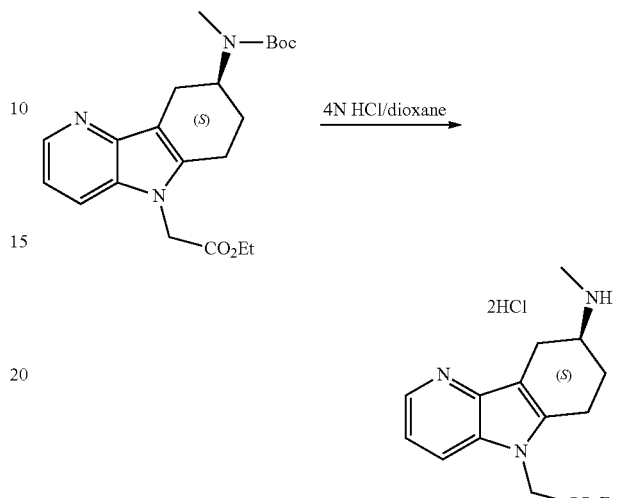

To (S)-ethyl 2-(8-((tert-butoxycarbonyl)(methyl)amino)-6,7,8,9-tetrahydro-5H-pyrido[3,2-b]indol-5-yl)acetate (100 mg, 0.258 mmol) was added 4N HCl in dioxane (0.895 mL). The reaction mixture was stirred at RT for 1 h and concentrated to give the desired product as a hydrochloride salt which can be used in the next step without further purification. LC-MS: t$_R$: 0.38 min./[M+H]$^+$: 288.25.

Biological Assays:

Preparation of hCRTH2 Receptor Membranes and Radioligand Displacement Assay:

First, recombinant HEK293-hCRTH2 cells were detached from culture plates into 5 ml buffer A/plate (Buffer A: 5 mM Tris, 1 mM MgCl$_2$-6H$_2$O pH=7.4) using a rubber policeman. Cells were then transferred into centrifugation tubes and centrifuged for 5 min at 400 g. The cell pellet was resuspended in the same buffer and tubes were frozen at 80° C. Cells were thawed and membrane fragments were generated by homogenization using a polytron homogenizer (30 seconds). The membrane fragments were then centrifuged at 3000 g for 20 minutes and resuspended in buffer C (Buffer C: 75 mM Tris, 25 mM MgCl$_2$, 250 mM Saccharose pH 7.4). Aliquots of membrane fragments were stored at −20° C.

Binding assay was performed in a final assay volume of 250 µl. First, 25 µl of test compound, previously diluted in Binding-Buffer (Binding-Buffer: 50 mM Tris-Base, 100 mM NaCl, 1 mM EDTA, 0.1% BSA (protease free), 0.01% NaN$_3$, 10 mM MnCl$_2$ pH 7.0) was placed into each well. After addition of 75 µl Binding-Buffer, 50 µl of the radio-ligand $^3$H-PGD$_2$ (at 2.5 nM (220.000 dpm/well) from ANAWA ART0662) was added to each well. Binding assay was started by addition of 100 µl CRTH$_2$ membrane fragments, reaching a final concentration of 20 µg/well. For non-specific binding, PGD$_2$ was added to the reaction mixture to 10 mM final concentration. This assay mix was incubated for 90 minutes at room temperature and then filtered through a GF/C filter 96-well plate which was pre-soaked for 3 hours in 0.5% polyethyleneimine (PEI). The filter-wells were washed three times with ice cold Binding-Buffer. Then, 40 µl of Microscint-40 (Packard) was added to each well and the retained radioactivity quantified in a Topcount (Packard).

Antagonistic activities of exemplified compounds are displayed in Table 2.

| Example | Name | IC$_{50}$ [nM] |
|---|---|---|
| 1 | 2-(8-((6-chlorobenzo[d]oxazol-2-yl)(methyl)amino)-6,7,8,9-tetrahydro-5H-pyrido[3,2-b]indol-5-yl)acetic acid | 11 |
| 2 | 2-(8-((5-chlorobenzo[d]oxazol-2-yl)(methyl)amino)-6,7,8,9-tetrahydro-5H-pyrido[3,2-b]indol-5-yl)acetic acid | 35 |
| 3 | 2-(8-((5-fluorobenzo[d]oxazol-2-yl)(methyl)amino)-6,7,8,9-tetrahydro-5H-pyrido[3,2-b]indol-5-yl)acetic acid | 31 |

Radioligand Displacement Assay-Human Serum Albumin (HSA):

Radioligand displacement assay in presence of human serum albumin (HSA) was performed as described above, with following modifications. Binding-Buffer-HSA: Binding-buffer+0.5% Sigma Albumin from Human serum A1887 (instead of 0.1% BSA). A volume of 25 µl test compound, previously diluted in Binding-BufferHSA was placed into each well. After addition of 75 µl Binding-Buffer-HSA, 50 µl of $^3$H-PGD$_2$ (at 2.5 nM (220.000 dpm/well) from ANAWA ART0662) was added to each well. Remaining protocol was identical as described above.

Antagonistic activities of exemplified compounds are displayed in Table 3.

| Example | Name | IC$_{50}$ [nM] |
|---|---|---|
| 1 | 2-(8-((6-chlorobenzo[d]oxazol-2-yl)(methyl)amino)-6,7,8,9-tetrahydro-5H-pyrido[3,2-b]indol-5-yl)acetic acid | 31 |

Eosinophil Shape Change Assay with human Plasma

After obtaining informed consent, blood samples were drawn by venipuncture according to the protocol approved by the ethics committee of Basel, Switzerland. Polymorphonuclear leukocytes (containing eosinophils, basophils and neutrophils) were isolated using the Polymorphprep™ method (Axis-Shield). In brief, anticoagulated whole blood was layered onto a Polymorphprep gradient (density 1.113 g/ml) and centrifuged at 500 g for 30 min. The polymorphonuclear cell fraction was harvested and depleted for erythrocytes by hypotonic saline lysis.

The polymorphonuclear cells were resuspended in assay buffer (1× PBS with Ca$^{2+}$/Mg$^{2+}$ supplemented with 0.1% BSA, 10 mM HEPES, and 10 mM Glucose, pH 7.4) at 5×10$^6$ cells/ml and stained with anti-CD49d-APC ((APC=Allophycocyanin) for 1 hour at RT. Test compounds, at various concentrations, were preincubated 10 min in human plasma (anticoagulated with a thrombin inhibitor). Then, human plasma was added to the polymorphonuclear cells to 50% of final assay volume with polymorphonuclear cells at 4×10$^6$ cells/ml. After incubation for 10 minutes at 37° C., the polymorphonuclear cells were activated for 5 min at 37° C. by addition of PGD2 at 100 nM final concentration. Activation was stopped by addition of 0.5 ml paraformaldehyde (1%).

Immediately after fixation with paraformaldehyde, the samples were analyzed by FACSCanto flow cytometer (BD Biosciences) and target cells were identified by their forward-scatter (FSC) and side-scatter (SSC) characteristics. Eosinophils were identified by the anti-CD49d-APC signal and their characteristic side-scatter (SSC) profile. Shape change responses, indicative of eosinophil activation, were quantified as the percent of cells with an increased forward-scatter.

Antagonistic activities of exemplified compounds are displayed in Table 6.

| Example | Name | IC$_{50}$ [nM] |
|---|---|---|
| 1 | 2-(8-((6-chlorobenzo[d]oxazol-2-yl)(methyl)amino)-6,7,8,9-tetrahydro-5H-pyrido[3,2-b]indol-5-yl)acetic acid | 27 |

Intracellular Calcium Mobilization Assay (FLIPR):

Cells (HEK-293), stably expressing the hCRTH2 receptor under the control of the cytomegalovirus promotor from a single insertion of the expression vector pcDNA5 (Invitrogen), are grown to confluency in DMEM (low glucose, Gibco) medium supplemented with 10% fetal calf serum (Bioconcept, Switzerland) under standard mammalian cell culture conditions (37° C. in a humidified atmosphere of 5% CO$_2$). Cells are detached from culture dishes using a dissociation buffer (0.02% EDTA in PBS, Gibco) for 1 min, and collected by centrifugation at 200 g at rt for 5 min in assay buffer (equal parts of Hank's BSS (HBSS, Bioconcept) and DMEM (low glucose, without phenol red, Gibco)). After incubation for 45 min (37° C. and 5% CO$_2$) in the presence of 1 µM Fluo-4 and 0.04% Pluronic F-127 (both Molecular Probes), and 20 mM HEPES (Gibco) in assay buffer, the cells are washed with and resuspended in assay buffer, then seeded onto 384-well FLIPR assay plates (Greiner) at 50,000 cells in 66 µl per well, and sedimented by centrifugation.

Stock solutions of test compounds are made up at a concentration of 10 mM in DMSO, and serially diluted in assay buffer to concentrations required for inhibition dose response curves. Prostaglandin D$_2$ (Biomol, Plymouth Meeting, PA) is used as an agonist.

A FLIPR Tetra instrument (Molecular Devices) is operated according to the manufacturers standard instructions, adding 4 µl of test compound dissolved at 10 mM in DMSO and diluted prior to the experiment in assay buffer to obtain the desired final concentration. 10 µl of 80 nM prostaglandin D$_2$ (Biomol, Plymouth Meeting, PA) in assay buffer, supplemented with 0.8% bovine serum albumin (fatty acid content<0.02%, Sigma), is then added to obtain a final concentration of 10 nM and 0.1%, respectively. Changes in fluorescence are monitored before and after the addition of test compounds at $\lambda_{ex}$=488 nm and $\lambda_{em}$=540 nm. Emission peak values above base level after prostaglandin D$_2$ addition are exported after base line subtraction. Values are normalized to high-level control (no test compound added) after subtraction of base line value (no prostaglandin D$_2$ added). The program XLlfit 3.0 (IDBS) is used to fit the data to a single site dose response curve of the equation $(A+((B-A)/(1+((C/x)^D))))$ and to calculate the IC$_{50}$ values.

In Vitro Cytotoxicity in Primary Cultured Rat Hepatocytes
  1. Methods
    1.1 Isolation and Culture of Rat Hepatocytes Adult male Wistar rats were narcotized with sodium pentobarbital and hepatocytes were isolated according to a standard procedure, i.e. by in situ perfusion of the liver with a collagenase solution. The viability of the purified hepatocytes, checked by the trypan blue dye exclusion method was greater than 85%. The isolated hepatocytes were resuspended in standard Williams Medium E, without phenol red, supplemented (WME supp.) with transferrin (100 μg/ml), triiodothyronine (10 μg/ml), gentamicin (50 μg/ml), hydrocortison hemisuccinate (13.36 μg/ml), glucagon (5 μg/ml), HEPES (10 mM), inosin (10 μ/ml), insulin (10 μg/ml), streptomycin (100 μg/ml) and penicillin (100 U/ml) and 10% fetal bovine serum (FBS). The cells were plated in collagen-coated 24-well plates at an initial density of 2×10$^5$ cells/well. After 4 h for attachment to the culture-plates, the medium was aspirated and replaced by fresh WME supp. without FBS containing the test compounds and incubated for 24 h at 37° C. in a 95% $O_2$ and 5% $CO_2$ atmosphere. For each experiment, i.e., with each batch of hepatocytes, treatments with the test compounds were done in quadriplicate. Quadriplicate controls (treatment with the vehicle only) were also present on each culture plate.

1.2 In Vitro Exposure to the Test Compounds

Stock solutions of the test compounds were prepared in DMSO a few hours before treatment start. Appropriate dilutions of these stock solutions were added to the culture media just prior to the treatment in order to give final concentrations of 0, 3, 10, 30, 100 and 300 μM. The final concentration of the vehicle DMSO was 1% (v/v).

1.3 Viability of the Cell Cultures 1.3.1 Monitoring of Monolayer Morphology

The morphology of the hepatocyte monolayers was monitored by light microscopy after 24 hours of exposure to the test compounds. Treatment related effects are described according to the following grading:

0 No morphological alterations observed upon treatment when compared to the control cultures 1-3 Treatment resulting in any morphological changes, e.g. intracellular granulation, vacuolization or cell death. Depending on the severity, these changes were regarded as slight (1), moderate (2) or strong (3).

K Treatment resulting in 100% dead cells and/or the complete detachment of the monolayer yielding a clear cell-free dish.

1.3.2 Leakage of Lactate Dehydrogenase

After 24 h treatment of the hepatocyte cultures, aliquots of culture medium were carefully collected and used for the analysis of lactate dehydrogenase (LDH) activity by spectrophotometry using the LDH cytotoxicity detection kit from Clontech (cat No. 630117, Mountain View, Calif., USA). For each experiment, additional cultures were used for the determination of total intracellular LDH activity at treatment start. For this purpose, 4 wells of cell culture per experiment were washed with cold saline before treatment start, sonicated in fresh medium and the homogenate was analyzed for total LDH activity. Enzyme activities in the culture media were assessed and expressed as percentage of the total activity present in the cultured hepatocytes at the beginning of the treatments.

2. Data Analysis

The lowest cytotoxic concentration (LCC) and the no effect concentration (NoEC) are given for each compound, based on cell morphology and LDH leakage after 24 h treatment. LCC is defined as the lowest concentration of the test compound leading to a clear effect on the cultured rat hepatocytes (morphology grading 2 or 2-fold increase in LDH leakage). A LCC value of >300 μM indicates the absence of effect on both endpoints at the highest test concentration of 300 μM. Compounds that exhibited only a slight cytotoxicity (morphology grading 1 or <2-fold increase in LDH leakage) at the highest test concentration were marked as "300 s". NoEC is defined as the highest test concentration of the compound which was without an effect on the cultured rat hepatocytes (morphology and LDH leakage).

3. Results

TABLE 7

LCC values of example compounds

| Example | LCC [μM] | NoEC [μM] |
|---|---|---|
| 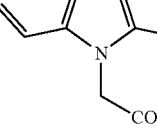 example 1 | >300 | >300 |
| 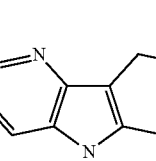 example 2 | 300s | 100 |
| 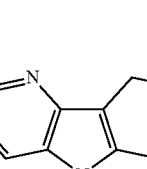 example 3 | 300s | 100 |
| 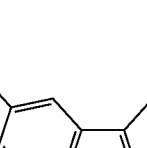 reference example (example 40 from WO 2011/117798) | 100 | 30 |

The invention claimed is:
1. A compound of formula (I):

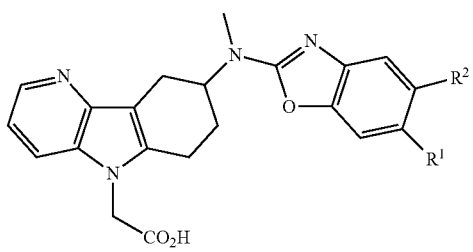

wherein
one of R¹ and R² represents hydrogen and the other one represents halogen;
or a salt thereof.

2. The compound according to claim 1, wherein R¹ represents halogen and R² represents hydrogen;
or a salt thereof.

3. The compound according to claim 1, wherein R¹ represents hydrogen and R² represents halogen;
or a salt thereof.

4. The compound of formula (I) according to claim 1, wherein the compound is a compound of formula ($I_{st1}$)

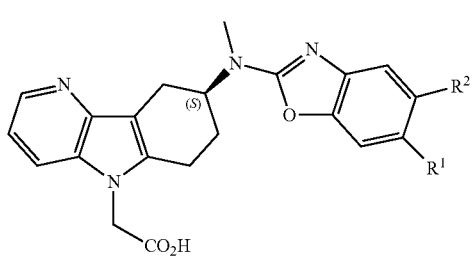

or a salt thereof.

5. The compound according to claim 1, wherein the compound is:
2-(8-((5-chlorobenzo [d] oxazol-2-yl)(methyl)amino)-6,7,8,9-tetrahydro-5H-pyrido [3,2-b]indol-5-yl)acetic acid;
2-(8-((5-fluorobenzo [d] oxazol-2-yl)(methyl)amino)-6,7,8,9-tetrahydro-5H-pyrido [3,2-b]indol-5-yl)acetic acid; or
2-(8-((6-chlorobenzo [d] oxazol-2-yl)(methyl)amino)-6,7,8,9-tetrahydro-5H-pyrido [3,2-b]indol-5-yl)acetic acid;
or a salt thereof.

6. The compound according to claim 1, wherein the compound is:
(S)-2-(8-((5-chlorobenzo [d] oxazol-2-yl)(methyl)amino)-6,7,8,9-tetrahydro-5H-pyrido [3,2-b]indol-5-yl)acetic acid;
(S)-2-(8-((5-fluorobenzo [d] oxazol-2-yl)(methyl)amino)-6,7,8,9-tetrahydro-5H-pyrido [3,2-b]indol-5-yl)acetic acid; or
(S)-2-(8-((6-chlorobenzo [d] oxazol-2-yl)(methyl)amino)-6,7,8,9-tetrahydro-5H-pyrido [3,2-b] indol-5-yl)acetic acid;
or a salt thereof.

7. A pharmaceutical composition comprising a compound according to claim 1, or a pharmaceutically acceptable salt thereof, and a pharmaceutically acceptable carrier.

8. The compound according to claim 1, or a pharmaceutically acceptable salt thereof, formulated as a medicament.

9. A method for treating a disease comprising administering to a subject in need thereof the compound according to claim 1, wherein the disease is a chronic or acute allergic disease.

10. A method for treating a disease comprising administering to a subject in need thereof the compound according to claim 1, wherein the disease is asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, anaphylactic shock, urticaria, eczema, or chronic obstructive pulmonary disease.

11. A method for treating a disease comprising administering to a subject in need thereof the compound according to claim 1, wherein the disease is small vessel vasculitides, eosinophilic esophagitis or eosinophilic cellulitis.

12. The method according to claim 11, wherein the small vessel vasculitide is Churg-Strauss syndrome.

* * * * *